(12) United States Patent
Morita et al.

(10) Patent No.: US 9,023,384 B2
(45) Date of Patent: May 5, 2015

(54) LIPOSOME AND METHOD FOR INJECTING SUBSTANCE TO CELL USING THIS LIPOSOME

(75) Inventors: Ikuo Morita, Tokyo (JP); Kazunari Akiyoshi, Tokyo (JP); Shinichiro Nomura, Tokyo (JP)

(73) Assignees: Tokyo Medical and Dental University, Tokyo (JP); Dai Nippon Printing Co., Ltd., Tokyo (JP)

( * ) Notice: Subject to any disclaimer, the term of this patent is extended or adjusted under 35 U.S.C. 154(b) by 1197 days.

(21) Appl. No.: 11/666,736

(22) PCT Filed: Nov. 2, 2005

(86) PCT No.: PCT/JP2005/020486
§ 371 (c)(1),
(2), (4) Date: Nov. 2, 2007

(87) PCT Pub. No.: WO2006/049307
PCT Pub. Date: May 11, 2006

(65) Prior Publication Data
US 2008/0279918 A1 Nov. 13, 2008

(30) Foreign Application Priority Data
Nov. 2, 2004 (JP) .................... 2004-319685

(51) Int. Cl.
| A61K 9/127 | (2006.01) |
| --- | --- |
| A61K 47/42 | (2006.01) |
| C12N 5/00 | (2006.01) |
| A61K 38/17 | (2006.01) |

(52) U.S. Cl.
CPC ............ *A61K 38/177* (2013.01); *A61K 9/127* (2013.01)

(58) Field of Classification Search
None
See application file for complete search history.

(56) References Cited

FOREIGN PATENT DOCUMENTS

| JP | 05-506253 A | 9/1993 |
| --- | --- | --- |
| JP | 8-504204 A | 5/1996 |
| JP | 3321622 B2 | 6/2002 |
| WO | WO 01/17511 A1 | 3/2001 |
| WO | 02/069896 A2 | 9/2002 |
| WO | 03/096981 A2 | 11/2003 |

OTHER PUBLICATIONS

Ahmad et al. Biochem. J. 339:247-253; 1999.*
Ahmad et al. Biochem J. 339, 247-253; 1999.*
Kim et al. J. Biol. Chem. 274:5581-5587; 1999.*
Moritani et al, Direct integration of cell-free-synthesized connexin-43 into liposomes and hemichannel formation. FEBS J. 277:3343-3352, 2010.*
Kaneda et al, Direct formation of proteo-liposomes by in vitro synthesis and cellular cytosolic delivery with connexin-expressing liposomes. Biomaterials 30:3971-3977, 2009.*
Ahmad S et al., "Synthesis and assembly of connexins in vitro into homomeric and heteromeric functional gap junction hemichannels", Biochemical Journal, vol. 339, No. 2, pp. 247 to 253 (1999), full text.
Kim D Y et al, "Gating Connexin 43 Channels Reconstituted in Lipid Vesicles by Mitogen-activated Protein Kinase Phosphorylation", The Journal of Biological Chemistry, vol. 274, No. 9, pp. 5581 to 5587 (1999).
Cell-free synthesis for analyzing the membrane integration, oligomerization, and assembly characteristics of gap junction connexins. Falk MM. Methods. (2000) 20(2):165-79.
Membrane insertion of gap junction connexins: polytopic channel forming membrane proteins. Falk MM, Kumar NM, Gilula NB. J Cell Biol. (1994) 127(2):343-55.
Extended European Search Report issued in corresponding application No. 05803421.6-2112 dated May 3, 2012.

* cited by examiner

*Primary Examiner* — Janet Epps-Smith
(74) *Attorney, Agent, or Firm* — Sughrue Mion, PLLC

(57) ABSTRACT

It is intended to efficiently inject into a target cell, a substance charged within a liposome. The present inventors have found that connexin synthesized within a liposome is introduced as connexon having a gap junction function into the liposome membrane. Specifically, the liposome according to the present invention is a liposome in which connexon composed of connexin synthesized by an in-vitro protein synthesis system is incorporated in a state of having a gap junction function.

9 Claims, 11 Drawing Sheets
(3 of 11 Drawing Sheet(s) Filed in Color)

Cx-U2OS / Cx-Lipo after 2h.

Cx-U2OS / noGENE-Lipo after 2h.

SEQUENCE LISTING

<160> NUMBER OF SEQ ID NOS: 3

<210> SEQ ID NO 1
<211> LENGTH: 1149
<212> TYPE: DNA
<213> ORGANISM: Homo sapiens
<220> FEATURE:
<221> NAME/KEY: CDS
<222> LOCATION: (1)..(1146)

<400> SEQUENCE: 1

```
atg ggt gac tgg agc gcc tta ggc aaa ctc ctt gac aag gtt caa gcc      48
Met Gly Asp Trp Ser Ala Leu Gly Lys Leu Leu Asp Lys Val Gln Ala
1               5                   10                  15 tac tca act gct gga ggg aag gtg tgg ctg tca gta ctt ttc att ttc      96
Tyr Ser Thr Ala Gly Gly Lys Val Trp Leu Ser Val Leu Phe Ile Phe
            20                  25                  30 cga atc ctg ctg ctg ggg aca gcg gtt gag tca gcc tgg gga gat gag     144
Arg Ile Leu Leu Leu Gly Thr Ala Val Glu Ser Ala Trp Gly Asp Glu
        35                  40                  45 cag tct gcc ttt cgt tgt aac act cag caa cct ggt tgt gaa aat gtc     192
Gln Ser Ala Phe Arg Cys Asn Thr Gln Gln Pro Gly Cys Glu Asn Val
    50                  55                  60 tgc tat gac aag tct ttc cca atc tct cat gtg cgc ttc tgg gtc ctg     240
Cys Tyr Asp Lys Ser Phe Pro Ile Ser His Val Arg Phe Trp Val Leu
65                  70                  75                  80 cag atc ata ttt gtg tct gta ccc aca ctc ttg tac ctg gct cat gtg     288
Gln Ile Ile Phe Val Ser Val Pro Thr Leu Leu Tyr Leu Ala His Val
                85                  90                  95 ttc tat gtg atg cga aag gaa gag aaa ctg aac aag aaa gag gaa gaa     336
Phe Tyr Val Met Arg Lys Glu Glu Lys Leu Asn Lys Lys Glu Glu Glu
            100                 105                 110 ctc aag gtt gcc caa act gat ggt gtc aat gtg gac atg cac ttg aag     384
Leu Lys Val Ala Gln Thr Asp Gly Val Asn Val Asp Met His Leu Lys
        115                 120                 125 cag att gag ata aag aag ttc aag tac ggt att gaa gag cat ggt aag     432
Gln Ile Glu Ile Lys Lys Phe Lys Tyr Gly Ile Glu Glu His Gly Lys
    130                 135                 140 gtg aaa atg cga ggg ggt ttg ctg cga acc tac atc atc agt atc ctc     480
Val Lys Met Arg Gly Gly Leu Leu Arg Thr Tyr Ile Ile Ser Ile Leu
145                 150                 155                 160 ttc aag tct atc ttt gag gtg gcc ttg ctg atc cag tgg tac atc          528
Phe Lys Ser Ile Phe Glu Val Ala Phe Leu Leu Ile Gln Trp Tyr Ile
                165                 170                 175 tat gga ttc agc ttg agt gct gtt tac act tgc aaa aga gat ccc tgc     576
Tyr Gly Phe Ser Leu Ser Ala Val Tyr Thr Cys Lys Arg Asp Pro Cys
            180                 185                 190 cca cat cag gtg gac tgt ttc ctc tct cgc ccc acg gag aaa acc atc     624
```

```
                Pro His Gln Val Asp Cys Phe Leu Ser Arg Pro Thr Glu Lys Thr Ile
                    195                 200                 205 ttc atc atc ttc atg ctg gtg gtg tcc ttg gtg tcc ctg gcc ttg aat       672
Phe Ile Ile Phe Met Leu Val Val Ser Leu Val Ser Leu Ala Leu Asn
210                 215                 220 atc att gaa ctc ttc tat gtt ttc ttc aag ggc gtt aag gat cgg gtt       720
Ile Ile Glu Leu Phe Tyr Val Phe Phe Lys Gly Val Lys Asp Arg Val
225                 230                 235                 240 aag gga aag agc gac cct tac cat gcg acc agt ggt gcg ctg agc cct       768
Lys Gly Lys Ser Asp Pro Tyr His Ala Thr Ser Gly Ala Leu Ser Pro
                245                 250                 255 gcc aaa gac tgt ggg tct caa aaa tat gct tat ttc aat ggc tgc tcc       816
Ala Lys Asp Cys Gly Ser Gln Lys Tyr Ala Tyr Phe Asn Gly Cys Ser
            260                 265                 270 tca cca acc gct ccc ctc tcg cct atg tct cct cct ggg tac aag ctg       864
Ser Pro Thr Ala Pro Leu Ser Pro Met Ser Pro Pro Gly Tyr Lys Leu
        275                 280                 285 gtt act ggc gac aga aac aat tct tct tgc cgc aat tac aac aag caa       912
Val Thr Gly Asp Arg Asn Asn Ser Ser Cys Arg Asn Tyr Asn Lys Gln
    290                 295                 300 gca agt gag caa aac tgg gct aat tac agt gca gaa caa aat cga atg       960
Ala Ser Glu Gln Asn Trp Ala Asn Tyr Ser Ala Glu Gln Asn Arg Met
305                 310                 315                 320 ggg cag gcg gga agc acc atc tct aac tcc cat gca cag cct ttt gat      1008
Gly Gln Ala Gly Ser Thr Ile Ser Asn Ser His Ala Gln Pro Phe Asp
                325                 330                 335 ttc ccc gat gat aac cag aat tct aaa aaa cta gct gct gga cat gaa      1056
Phe Pro Asp Asp Asn Gln Asn Ser Lys Lys Leu Ala Ala Gly His Glu
            340                 345                 350 tta cag cca cta gcc att gtg gac cag cga cct tca agc aga gcc agc      1104
Leu Gln Pro Leu Ala Ile Val Asp Gln Arg Pro Ser Ser Arg Ala Ser
        355                 360                 365 agt cgt gcc agc agc aga cct cgg cct gat gac ctg gag atc tag           1149
Ser Arg Ala Ser Ser Arg Pro Arg Pro Asp Asp Leu Glu Ile
    370                 375                 380

<210> SEQ ID NO 2
<211> LENGTH: 382
<212> TYPE: PRT
<213> ORGANISM: Homo sapiens

<400> SEQUENCE: 2

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
                20                  25                  30

Arg Ile Leu Leu Leu Gly Thr Ala Val Glu Ser Ala Trp Gly Asp Glu
            35                  40                  45

Gln Ser Ala Phe Arg Cys Asn Thr Gln Gln Pro Gly Cys Glu Asn Val
        50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
                100                 105                 110

Leu Lys Val Ala Gln Thr Asp Gly Val Asn Val Asp Met His Leu Lys
            115                 120                 125
```

```
Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
                180                 185                 190

Pro His Gln Val Asp Cys Phe Leu Ser Arg Pro Thr Glu Lys Thr Ile
            195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380

<210> SEQ ID NO 3
<211> LENGTH: 11
<212> TYPE: PRT
<213> ORGANISM: Homo sapiens

<400> SEQUENCE: 3

Thr Ala Leu Asp Trp Ser Trp Leu Gln Thr Glu
1               5                   10
```

LIPOSOME AND METHOD FOR INJECTING SUBSTANCE TO CELL USING THIS LIPOSOME

TECHNICAL FIELD

The present invention relates to a liposome used in so-called drug delivery systems and general biochemical experiments and to a method of injecting a substance into a cell using the same.

BACKGROUND ART

The overview of a drug delivery system (hereinafter, referred to as DDS) using liposomes can be understood with reference to Non-Patent Document 1. Examples of a primary problem of the DDS using liposomes can include low efficiency of administration of drugs charged within liposomes. Examples of one approach to solve this problem can include an approach by which tropism targeted to target cells such as cancer cells is imparted to liposomes. For example, an approach has been developed by which a liposome in which a sugar chain that specifically recognizes lectin (sugar chain-recognizing protein) is introduced in the membrane is used to control the target tropism of the liposome.

However, the approach for improving the target tropism of a liposome is an approach that focuses on the interaction between liposomes and target cells, but not an approach that focuses on the mechanism of action by which drugs charged within liposomes are transferred to target cells. Thus, the conventional approach still has the problem of low efficiency of administration of drugs charged within liposomes.

On the other hand, examples of documents that disclose the introduction of proteins into liposome membranes can include Non-Patent Documents 2 and 3. These Non-Patent Documents 2 and 3 use as a protein to be introduced, connexin that constitutes a gap junction serving as an intercellular substance transfer pathway.

Non-Patent Document 2 has disclosed that connexin 26 is synthesized in a cell-free system and then incorporated into a liposome. However, Non-Patent Document 2 has disclosed that a hemichannel, which is formed in the connexin 26-incorporated liposome, causes ascorbic acid charged within the liposome to be leaked out from the hemichannel. Hence, the liposome disclosed in Non-Patent Document 2 seems to be impossible to use in DDS using liposomes within which drugs or the like are charged.

Alternatively, Non-Patent Document 3 has disclosed that connexin 43 generated within a cell is purified and incorporated into a liposome membrane. Non-Patent Document 3 has particularly disclosed that dephosphorylation using CIP treatment after the connexin 43 incorporation into the liposome increases permeability. The phosphorylated site of connexin is present within the cell, and the treatment uses an enzyme (CIP) of 1500 or higher in molecular weight. This means that connexin is incorporated so that a site supposed to be present within a cell is positioned outside of a liposome membrane.

Attempts to introduce connexin into liposome membranes can be illustrated as described above. However, no documents have disclosed a liposome in which connexon is incorporated in a state of having a gap junction function.

Non-Patent Document 1: D. D. Lasic et al., "liposomes: from basic to applications" Elsevier Science Publishers, (1993)

Non-Patent Document 2: Ahmad S, Evans W H. "Post-translational integration and oligomerization of connexin 26 in plasma membranes and evidence of formation of membrane pores: implications for the assembly of gap junctions." (2002) Biochem. J. 365: 693-699.

Non-Patent Document 3: Doo Yeon Kim, et al., "Gating Connexin 43 Channels Reconstituted in Lipid Vesicles by Mitogen-activated Protein Kinase Phosphorylation" (1999) J. Biol. Chem. 274 No. 9, pp. 5581-5587

DISCLOSURE OF THE INVENTION

Thus, in light of the circumstances described above, an object of the present invention is to provide a liposome that can very efficiently inject a substance charged therewithin into a target cell and to provide a method of injecting a substance into a cell using this liposome.

The present inventors have conducted diligent studies for attaining the object. As a result, the present inventors have successfully synthesized connexin in the presence of a liposome and have completed the present invention by finding out that, surprisingly, the connexin thus synthesized is introduced as connexon having a gap junction function into the liposome membrane.

Specifically, the present invention encompasses the following inventions:

(1) A liposome in which connexon composed of connexin synthesized by an in-vitro protein synthesis system is incorporated in a state of having a gap junction function.

(2) The liposome according to (1), characterized in that the connexin is connexin 43.

(3) The liposome according to (1), characterized in that a protein having an ability to bind to a particular cell is further incorporated therein.

(4) The liposome according to any of (1) to (3), characterized in that the liposome further comprises an intended substance therewithin.

(5) The liposome according to (4), characterized in that the intended substance is a physiologically active component.

(6) The liposome according to (4), characterized in that the intended substance is mainly composed of a component of 1500 or lower in molecular weight.

(7) A method for injecting a substance to a cell, comprising:

bringing a liposome according to any of (4) to (6) into contact with an isolated cell or cultured cell; and injecting the intended substance into the isolated cell or cultured cell.

(8) A method for treating disease, comprising the step of administering a liposome according to (5).

The present specification encompasses the contents described in the specification and/or drawings of Japanese Patent Application No. 2004-319685 that serves as a basis for the priority of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
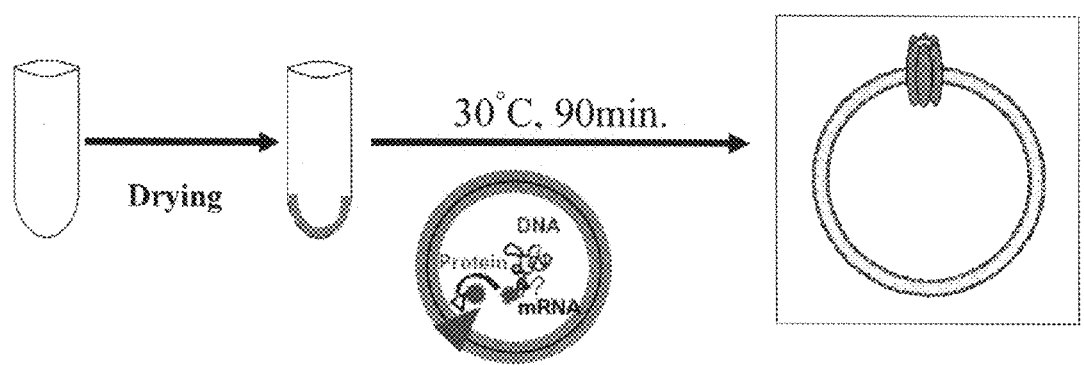
FIG. 1 is a diagram schematically showing a method for producing a liposome in which connexon is incorporated in the membrane.

Hereinafter, a liposome and a method for injecting a substance to a cell according to the present invention will be described in detail with reference to drawings.

1. Liposome

The liposome according to the present invention is a liposome in which connexon composed of connexin synthesized by an in-vitro protein synthesis system is incorporated in a state of having a gap junction function.

Liposomes originally mean closed vesicles composed of a lipid assembly in a membrane form and an aqueous phase within the membrane (see D. D. Lasic et al., "liposomes: from basic to applications" Elsevier Science Publishers, p. 1-171 (1993)). Thus, the liposome according to the present invention comprises connexon having a gap junction function, which is introduced within the membrane mainly composed of lipid.

In this context, examples of the lipid of the liposome can include glyceroglycolipid, sphingoglycolipid, cholesterol, and phospholipid known in the art.

Examples of the glyceroglycolipid can include sulfoxyribosyl glyceride, diglycosyl diglyceride, digalactosyl diglyceride, galactosyl diglyceride, and glycosyl diglyceride. Examples of the sphingoglycolipid can include galactosyl cerebroside, lactosyl cerebroside, and ganglioside.

Examples of the phospholipid can include natural or synthetic phospholipid such as phosphatidylcholine, phosphatidylethanolamine, phosphatidylserine, phosphatidic acid, phosphatidylglycerol, phosphatidylinositol, lysophosphatidylcholine, sphingomyelin, egg yolk lecithin, soybean lecithin, and hydrogenated phospholipid.

Examples of the phosphatidylcholine can include soybean phosphatidylcholine, egg yolk phosphatidylcholine, dilauroylphosphatidylcholine, dimyristoylphosphatidylcholine, dipalmitoylphosphatidylcholine, and distearoylphosphatidylcholine. Examples of the phosphatidylethanolamine can include dioleoylphosphatidylethanolamine, dilauroylphosphatidylethanolamine, dimyristoylphosphatidylethanolamine, dipalmitoylphosphatidylethanolamine, and distearoylphosphatidylethanolamine. Examples of the phosphatidylserine can include dilauroylphosphatidylserine, dimyristoylphosphatidylserine, dipalmitoylphosphatidylserine, and distearoylphosphatidylserine. Examples of the phosphatidylglycerol can include dilauroylphosphatidylglycerol, dimyristoylphosphatidylglycerol, dipalmitoylphosphatidylglycerol, and distearoylphosphatidylglycerol. Examples of the phosphatidylinositol can include dilauroylphosphatidylinositol, dimyristoylphosphatidylinositol, dipalmitoylphosphatidylinositol, and distearoylphosphatidylinositol.

The liposome used in the present invention is not particularly limited. Examples of preferable liposomes can include those comprising molecules actually constituting biomembranes and forming a liquid crystalline phase at room temperature. The lipid bilayer membrane when formed from pure substances has two phases, a gel phase and a soft liquid crystalline phase, depending on temperatures and exhibits phase transition attributed to changes in temperature. The membranes of live cells are mixtures but are regarded as being in a liquid crystalline state.

The liposome that can be used generally has a size of 20 nm to 100 μm, preferably 200 nm to 10 μm, and is more preferably GV (Giant Vesicle), which is easy to separate by centrifugation procedures described later. In this context, GV means a phospholipid bilayer membrane vesicle of 1 μm or larger in diameter.

The liposome is a particle composed of artificial lipid membranes and is formed as a lipid bilayer made of phospholipid, glyceroglycolipid, cholesterol, or the like. A wide range of methods known in the art such as surfactant removal, hydration, ultrasonic, reverse phase distillation, freezing and thawing, ethanol injection, extrusion, and high-pressure emulsification methods are applied to the preparation of the liposome. Details of the preparation of the liposome is described in JP Patent Publication (Kokai) No. 9-208599A (1997) and so on. For example, gel filtration, dialysis, and ultrafiltration are generally used as the surfactant removal method.

A wide range of connexin known in the art can be used as the connexin of the present invention without particular limitations. Connexin is a protein that constitutes a gap junction involved in intercellular communication. A connexin hexamer constitutes connexon.

Examples of the connexin can include connexin 46, connexin 43, connexin 37, connexin 40, connexin 50, connexin 32, connexin 26, connexin 31, connexin 31.1, connexin 45, connexin 30, connexin 36, connexin 62, connexin 31.9, and connexin 40.1.

Among the connexin species listed above, the connexin 43, which plays a key role in an intercellular gap junction, is particularly preferably used in the present invention. The base sequence and amino acid sequence of connexin 43 are shown in SEQ ID NOS: 1 and 2, respectively. The base sequence and amino acid sequence represented by SEQ ID NOS: 1 and 2 are from connexin 43 derived from humans. Connexin 43 derived from mice and rats can also be used in the present invention.

The liposome according to the present invention may optionally comprise as components other than the lipid and connexin: a membrane stabilizer such as sterols (e.g., cholesterol), cholesterol ester, glycerin fatty acid ester (e.g., triolein and trioctanoin), polyglycerin fatty acid ester, and free fatty acid; an antioxidant such as tocopherol; and a charged substance such as stearylamine, dicetyl phosphate, and ganglioside. The amount of these additives formulated is not particularly limited and is preferably approximately 0.1 to 20% (w/w) with respect to the total amount of the lipid forming the liposome.

Furthermore, the liposome according to the present invention may be coated for the purpose of circumventing the uptake into reticular systems when administered into living bodies. In this context, the coating encompasses not only the coating of the liposome itself but also a state in which a lipid derivative having an appropriate substituent is mixed as a coating agent into raw material lipid for the liposome to thereby position the substituent in the outer layer of the liposome as if the whole liposome is coated. Examples of the coating agent include polyethylene glycol-lipid derivatives described in FEBS Lett. 268, 235 (1990), polyoxyethylene derivatives described in JP Patent Publication (Kohyo) No. 3-507024A (1991), and glucuronic acid-lipid derivatives described in Biochim. Biphys. Acta, 1126, 1992. The amount of the coating agent used can be selected appropriately from amounts that can maintain the lipid bilayer membrane structure of the liposome, and is preferably, for example, approximately 1 to 10% (w/w) with respect to the total amount of the lipid forming the liposome. Moreover, a method for the coating can be performed by a method known per se in the art.

Furthermore, the liposome according to the present invention may comprise a substance that improves particular cell (target cell) tropism for the purpose of specifically injecting a substance to the particular cell. Examples of the substance that improves target cell tropism can include, but not particularly limited to: antibodies; antibody fragments; sugar chains as ligands against sugar chain receptors on cell surfaces, such as glucose, galactose, mannose, and fucose; sialic acid and derivatives thereof; transferrin and derivatives thereof as ligands against peptide receptors on cell surfaces; and folic acid derivatives against folic acid receptors.

The liposome according to the present invention comprises an intended substance therewithin. In this context, the intended substance means a compound intended to be injected into a cell. Examples of the intended substance can include, but not limited by any means to, compounds having a known function as an active drug ingredient, organic compounds, nucleic acids, peptides, and compounds having an unknown function. Moreover, the intended substance is injected into a cell via the connexon incorporated in the liposome membrane. Therefore, the intended substance has a molecular weight level that can pass through the connexon and is preferably, for example, of 1500 or lower in molecular weight.

Such a substance is not particularly limited as long as it is any compound or substance composition that can be administered to animals, preferably humans. For example, the substance encompasses compounds or compositions that exert physiological activity in vivo and are effective for preventing or treating disease, for example, compounds or compositions used in diagnosis, such as contrast agents, and further encompasses even genes useful for gene therapy. Examples of the physiologically active component can include preventive and therapeutic agents for osteopathy or joint disease known in the art, such as calcium agents, active vitamin D3 (e.g., 1α-hydroxyvitamin D3, 1α-2,5-dihydroxyvitamin D3, flocalcitriol, and secalciferol), calcitonin and derivatives thereof, peptides, β-alanyl-3,4-dihydroxyphenylalanine, xanthine derivatives, thrombomodulin, 17β-estradiol, steroid hormones (e.g., norethindrone), polyphenol compounds, prostaglandins, and interferon. Moreover, examples of the substance can include: central analgesics such as morphine, codeine, and pentazocine; steroid agents such as prednisolone, dexamethasone, and betamethasone; nonsteroidal anti-inflammatory agents such as aspirin, indomethacin, loxoprofen, and diclofenac sodium; and antiphlogistic analgesics such as antiphlogistic enzymes (e.g., bromelain, lysozyme, and protease). Further examples of the substance can include antirheumatic drugs such as sodium aurothiomalate, auranofin, D-penicillamine, bucillamine, lobenzarit, actarit, and salazosulfapyridine. Further alternative examples of the substance can include: immunosuppressive agents such as methotrexate, cyclophosphamide, azathioprine, and mizoribine; antiviral agents such as acyclovir, zidovudine, and interferons; antimicrobial agents such as aminoglycoside, cephalosporin, and tetracycline; polyene antibiotics; and antifungal agents such as imidazole and triazole. Examples of the substance can additionally include sterols (e.g., cholesterol), carbohydrate (e.g., sugar and starch), cell receptor proteins, immunoglobulin, enzymes, hormone, neurotransmitters, glycoproteins, peptides, proteins, dyes, radioactive labels (e.g., radioisotopes and radioisotope-labeled compounds), radiopaque compounds, fluorescent compounds, bronchodilators, and local anesthetics.

The liposome according to the present invention particularly preferably comprises antitumor agents. Examples of the antitumor agents include, but not particularly limited to, alkylating agents, antimetabolites of various types, antitumor antibiotics and other antitumor agents, antitumor plant components, BRM (biologically responsive modifier), antiangiogenic agents, cell adhesion inhibitors, matrix metalloprotease inhibitors, and hormone.

More specifically, examples of the alkylating agents can include: chloroethylamine alkylating agents such as nitrogen mustard, nitrogen mustard N-oxide, ifosfamide, melphalan, cyclophosphamide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, chlorozotocin, and ranimustine; sulfonic esters such as busulfan, improsulfan tosilate, and piposulfan; and dacarbazine and procarbazine.

Examples of the antimetabolites of various types can include: purine antimetabolites such as 6-mercaptopurine, azathioprine, 6-thioguanine, and thioinosine; pyrimidine antimetabolites such as fluorouracil, tegafur, tegafur-uracil, carmofur, doxifluridine, broxuridine, cytarabine, and enocitabine; folic acid antimetabolites such as methotrexate and trimetrexate; and salts or complexes thereof.

Examples of the antitumor antibiotics can include: anthracycline antitumor antibiotics such as daunorubicin, aclarubicin, doxorubicin, pirarubicin, and epirubicin; actinomycin antitumor antibiotics such as actinomycin D; chromomycin antitumor antibiotics such as chromomycin A3; mitomycin antitumor antibiotics such as mitomycin C; bleomycin antitumor antibiotics such as bleomycin and peplomycin; and salts or complexes thereof. Examples of the other antitumor agents can include cisplatin, carboplatin, tamoxifen, L-asparaginase, aceglatone, sizofuran, picibanil, ubenimex, and krestin, and salts or complexes thereof.

Examples of the antitumor plant components can include: plant alkaloids such as camptothecine, vindesine, vincristine, and vinblastine; epipodophyllotoxines such as etoposide and teniposide; and salts or complexes thereof. Alternatively, pipobroman, neocarzinostatin, and hydroxyurea can also be used. Examples of the BRM can include tumor necrosis factors and indomethacin, and salts or complexes thereof. Examples of the antiangiogenic agents can include fumagillol derivatives and salts or complexes thereof. Examples of the cell adhesion inhibitors can include substances having RGD sequences and salts or complexes thereof. Examples of the matrix metalloprotease inhibitors can include marimastat and batimastat, and salts or complexes thereof. Examples of the hormone can include hydrocortisone, dexamethasone, methylprednisolone, prednisolone, prasterone, betamethasone, triamcinolone, oxymetholone, nandrolone, metenolone, fosfestrol, ethinylestradiol, chlormadinone, and medroxyprogesterone, and salts or complexes thereof.

Examples of a method for producing the liposome according to the present invention can include a method by which an in-vitro protein synthesis system for synthesizing connexin and a liposome reconstitution system for forming the liposome are allowed to proceed simultaneously. In this context, the in-vitro protein synthesis system is also called a cell-free protein synthesis system and means a system in which transcriptional reaction and translational reaction are coupled in one tube to synthesize proteins. For example, in an Eppendorf tube, cell extracts, substrates (nucleotides and amino acids) necessary for protein synthesis, buffer solutions, salts, connexin-encoding DNA, and RNA polymerase are mixed and heated to an appropriate temperature. As a result, transcriptional and translational reactions occur to synthesize proteins encoded by the template. Rabbit reticulocyte and wheat germ cell extracts can be used as the cell extracts. Alternatively, the liposome reconstitution system is, for example, a system in which lipid is dissolved in an organic solvent such as diethyl ether, isopropyl ether, or chloroform and then prepared into a thin membrane by the removal of the organic solvent by evaporation under reduced pressure, and the thin membrane is supplemented with an active ingredient aqueous solution and mixed at a temperature slightly higher than the phase transition temperature to thereby construct a liposome.

In the method for producing the liposome according to the present invention, the active ingredient aqueous solution in the liposome reconstitution system is supplemented with components necessary for in-vitro protein synthesis and also supplemented with the intended substance to be charged within the liposome. Thereby, the components necessary for the in-vitro protein synthesis system and the intended substance can be charged into the reconstituted liposome. Specifically, in the method for producing the liposome according to the present invention, connexin is synthesized in the presence of the liposome by in-vitro protein synthesis. After connexin synthesis by the in-vitro protein synthesis system present within the liposome, the synthesized connexin forms a hexamer. As a result, connexon, which is the connexin hexamer, is present in the liposome membrane.

Specifically, a 50 µL aliquot of egg yolk phosphatidylcholine (manufactured by Nacalai Tesque, Inc.) as lipid dissolved at a concentration of 5 mM in an organic solvent (a solvent of chloroform and methanol adjusted to a 2:1 ratio by volume) is initially collected into a round-bottomed test tube, followed by solvent evaporation under argon flow. A structure formed in the bottom of the test tube by this procedure is referred to as a dry lipid film. Next, 50 µL of rabbit reticulocyte cell extracts (TNT Quick Coupled transcription/translation Systems; Promega) for in-vitro protein synthesis is prepared. This solution is mixed with an intended substance. To this mixture solution, for example, a connexin 43 gene-encoding plasmid is added and gently stirred. Immediately thereafter, the solution is added to the dry lipid film. In this procedure, the final lipid concentration is adjusted to 5 mM. This test tube is hermetically sealed and immediately placed in an incubator at 37° C. The test tube is left standing for 90 minutes and then cooled to 4° C. This procedure brings about liposome formation, the incorporation of connexin into the liposome membrane, and the encapsulation of the intended substance into the liposome to thereby obtain a liposome suspension.

The method for producing the liposome according to the present invention is not limited to the methods described above. A method known in the art can be used. For example, lipid is dissolved in an organic solvent such as diethyl ether, isopropyl ether, or chloroform and then emulsified after the addition of an active ingredient aqueous solution to obtain a W/O emulsion. The organic solvent can be removed by evaporation under reduced pressure at an appropriate temperature to obtain a reverse-phase evaporation vesicle (REV). Examples of other methods for producing the liposome include a stable plurilamellar vesicle (SPLV) method [JP Patent Publication (Kohyo) No. 59-500952A (1984) (WO83/03383)] and a dehydration-rehydration vesicle method [C. Kirby et al., Biotechnology, Nov. issue, 979 (1984)]. For a fat-soluble and low water-soluble intended substance, the intended substance can be dissolved in the lipid organic solvent described above and thereby contained within the liposome. The liposome thus obtained can be adjusted to a preferable particle size by forced sieving or the like. The liposome thus obtained may be used directly, and however, is preferably used after the separation and removal of free active ingredients uncontained in the liposome by, for example, centrifugation, gel filtration, or dialysis.

In the more specific method for producing the liposome, for example, components necessary for an in-vitro protein synthesis system, an intended substance, and lipid are dissolved in chloroform in advance. Then, a lipid film is formed on a glass wall according to the method of Bangham et al. [J. Mol. Biol. 13, 238, 1965] and hydrated by the addition of water thereto to prepare a multilamellar vesicle (MLV). The obtained multilamellar vesicle (MLV) can further be subjected to forced sieving using a filter with a particular pore size to thereby obtain a liposome dispersion having particular particle size distribution. The pore size of the filter for forced sieving is appropriately adjusted depending on the desired particle size of the liposome. The pore size is, for example, approximately 20 to 100,000 nm, preferably approximately 50 to 10,000 nm, more preferably approximately 50 to 5,000 nm, even more preferably approximately 100 to 500 nm.

The obtained liposome dispersion may be used directly or may be supplemented with additives such as sugars, polyhydric alcohol, water-soluble polymers, nonionic surfactants, antioxidants, pH adjustors, and hydration promoters. The liposome preparation dispersion supplemented with the additives may be prepared into a dry liposome by drying (e.g., freeze drying or spray drying). The liposome of the present invention also encompasses these dry liposomes. Examples of a method for drying the liposome dispersion include a method described in JP Patent Publication (Kokai) No. 64-3115A (1989) by which a liposome dispersion is supplemented with sugar and freeze-dried. General conditions used in the freeze drying of preparations are used as the conditions of the freeze drying. The addition of additives other than sugar can also be performed according to the method described in JP Patent Publication (Kokai) No. 64-3115A (1989). As a result of the drying, the additives are dispersed as a powdered medium in the dry liposome. The content of the powdered medium in the dry liposome preparation is preferably approximately 1 to 1000 parts by weight, more preferably approximately 50 to 500 parts by weight, with respect to 100 parts by weight of the liposome. The dry liposome is supplemented with water, a saline, a buffer solution such as phosphate, citrate, and acetate buffer solutions (preferably water) as an aqueous medium and thereby prepared into a liposome dispersion, which can be used as an injection. The aqueous medium may be supplemented with the additives in advance. The liposome dispersion thus obtained may be used directly or may be supplemented with the additives. The additives are preferably added, into the liposome dispersion, at a concentration that is adjusted so that relative osmotic pressure with respect to physiological osmotic pressure is approximately 0.8 to 10 times the osmotic pressure of the aqueous medium in the internal phase of the liposome. For example, the sugars are added at a concentration of, for example, approximately 0.1 to 100% (W/W), preferably approximately 1 to 20% (W/W), into the liposome dispersion.

Examples of the sugars as the additives include monosaccharides (e.g., mannitol, glucose, glucosamine, and sorbitol), disaccharides (e.g., trehalose, lactose, and sucrose), and tri or higher polysaccharides (e.g., glucosamineglycan, hyaluronic acid, dextran, dextran sulfate, chondroitin, and chondroitin sulfate). Examples of the polyhydric alcohols as the additives include glycerin and polyethylene glycol. Examples of the water-soluble polymers as the additives include polyvinyl alcohol (PVA). Examples of the nonionic surfactants as the additives include Pluronic, HCO-50, HCO-60, Tween 20, and Tween 80. Examples of the antioxidants as the additives include ascorbic acid. Examples of the pH adjustors as the additives include glycine, ammonium acetate, citric acid, hydrochloric acid, and sodium hydroxide. Examples of the hydration promoters as the additives include compounds having a thickening property and a water absorbing property, such as self-crosslinked polyacrylic acid and water-soluble cellulose derivatives. Of these additives, preferably sugars, more preferably monosaccharides (even more preferably mannitol) or disaccharides (even more preferably trehalose) are used.

2. Method for Injecting Substance Using Liposome

The liposome according to the present invention described in the paragraph 1 can be used in general biochemical experiments for the purpose of injecting an intended substance to cells having connexon in the cell membranes. Animal cells, insect cells, plant cells, and so on usually used in the art can be used as the cells without particular limitations. Examples of the animal cells can include in-vitro cultured animal cells and/or animal tissues and more specifically can include COS cells, CHO cells, antibody-producing fused cells typified by mouse-human, mouse-mouse, and mouse-rat hybridomas, BHK cells, and HeLa cells.

A solution containing the liposome is brought into contact with an isolated cell or cultured cell. Solutions prepared by the method for producing the liposome as described above can be used as the solution containing the liposome. Specifically, a solution containing the produced liposome can be used in which a Cx43-encoding plasmid with a T7 promoter is added in an amount of 1 µg per 50 µL of an in-vitro solution to a mixture solution of rabbit reticulocyte lysates (kit product in the form of master mix) containing RNA polymerase, amino acids serving as raw materials, an RNase inhibitor, and so on and adjusted to the final concentration of lipid (raw material for the liposome) of 5 mM. The liposome used preferably comprises a molecule actually constituting biomembranes. For example, egg yolk lecithin is used. The liposome more preferably has a size of GV (Giant Vesicle) of 1 µm or larger in diameter, which is easy to separate by centrifugation procedures described later. It is desired that all the adjustments and reactions should be performed on ice in a clean bench. Other conditions can be set according to the protocol of an in-vitro expression kit. Calcein and an NBD peptide used in Examples below were diluted with sterilized purified water for use.

Conditions for bringing the solution containing the liposome into contact with the cell involve gradually adding 10 to 20 µL of the liposome solution per mL of a culture solution. The mixture is incubated under usual culture conditions of 5% $CO_2$ and 37° C. Detailed investigation has not been performed as to the influence of addition of the in-vitro solution on pH, salt concentrations, and components contained in the expression solution. However, no changes have been observed in cell morphology even by culture for 48 hours or longer after the addition, indicating no toxicity.

The use of the liposome according to the present invention can very efficiently inject an intended substance to cells. Particularly, connexon in the membrane of the liposome according to the present invention is synthesized by the in-vitro protein synthesis system and therefore, is not phosphorylated. Connexon in cells is generally known to have its substance permeability suppressed by phosphorylation and increased by dephosphorylation. However, the liposome according to the present invention can maintain the internal intended substance without transmitting the intended substance to the outside, in spite of the fact that connexon therein is not phosphorylated. Only when the connexon in the membrane of the liposome according to the present invention forms a gap junction with connexon present in a target cell membrane, the intended substance within the liposome is transferred to the target cell. As described above, the liposome according to the present invention is a totally unprecedented novel liposome in which connexon having a gap junction function is incorporated in the membrane.

3. Use of Liposome as Therapeutic Agent and Treatment Method Using Liposome

The liposome according to the present invention comprises an active drug ingredient therewithin and can thereby be used as a liposome preparation, as described above. In other words, the liposome according to the present invention can be used in the treatment of disease and can be used in novel treatment methods.

The liposome dispersion containing a physiologically active component as an intended substance may be used directly as a pharmaceutical composition containing the liposome according to the present invention or may be supplemented with additives such as sugars, polyhydric alcohol, water-soluble polymers, nonionic surfactants, antioxidants, pH adjustors, and hydration promoters. Alternatively, the liposome dispersion or the liposome dispersion supplemented with the additives may be prepared into a dry liposome preparation by drying (e.g., freeze drying or spray drying). The pharmaceutical composition containing the liposome according to the present invention also encompasses these dry liposome preparations. Examples of a method for drying the liposome dispersion include a method by which the liposome dispersion is supplemented with sugar and so on and freeze-dried under general conditions used in the freeze drying of usual preparations. The dry liposome preparation is supplemented with water, a saline, or a buffer solution such as phosphate, citrate, and acetate buffer solutions and thereby prepared into a liposome dispersion, which can be used as a liquid preparation such as an injection. The liposome dispersion thus obtained may be used directly or may be supplemented with the additives or pharmacologically acceptable excipients for use. The additives are preferably added, into the liposome dispersion, at a concentration that is adjusted to be physiological osmotic pressure. Alternatively, the dry liposome preparation may be used as a solid preparation (e.g., a granule or tablet) either directly or together with pharmacologically acceptable excipients.

The pharmaceutical composition containing the liposome according to the present invention is usually produced by mixing the liposome with pharmacologically acceptable excipients according to a method known in the art [routine method in the art of pharmaceutical techniques, e.g., methods described in Japanese Pharmacopoeia (e.g., 13th Edition)]. Examples of the pharmacologically acceptable excipients used include a variety of organic or inorganic excipient substances routinely used as pharmaceutical raw materials, such as: lubricants, binders, and disintegrants for solid preparations; and solvents, solubilizers, suspending agents, tonicity agents, buffers, and soothing agents for liquid preparations. Moreover, pharmaceutical additives such as surfactants, foaming agents, dyes, acidity agents, antiseptics, antioxidants, coloring agents, sweeteners, and flavoring agents can be used if needed.

More specific examples of the pharmacologically acceptable excipients include: inorganic salt excipients such as calcium citrate and calcium phosphate; lubricants such as magnesium stearate, calcium stearate, light anhydrous silicic acid, and hydrous silicon dioxide; binders such as hydroxypropylcellulose, hydroxypropylmethylcellulose, pregelatinized starch, polyvinyl alcohol, polyvinyl pyrrolidone, gum arabic powders, gelatin, and pullulan; and disintegrants such as celluloses (e.g., low-substituted hydroxypropylcellulose and crystalline cellulose), a variety of starches or starch derivatives (e.g., corn starch, partially pregelatinized. starch, and hydroxypropylstarch), crospovidone, and bentonite.

Alternative examples thereof include: solvents such as salt solutions, glucose solutions, and mixtures of salt solutions and glucose solutions; solubilizers such as dextran, polyvinyl pyrrolidone, sodium benzoate, ethylenediamine, salicylic acid amide, nicotinic acid amide, and polyoxyethylene hydrogenated castor oil derivatives; buffers such as borate buffers, phosphate buffers, citrate buffers, tartrate buffers, and acetate buffers; and soothing agents such as albumin, polyhydric alcohols (e.g., glycerin and propylene glycol), lidocaine hydrochloride, and benzyl alcohol.

Further examples thereof include: surfactants such as sorbitan fatty acid ester, polyoxyethylene fatty acid ester, phospholipid, glycerin fatty acid ester, polyethylene glycol fatty acid ester, polyoxyethylene hydrogenated castor oil, polyoxyethylene alkyl ether, and sucrose fatty acid ester; foaming agents such as sodium hydrogen carbonate, sodium carbonate, and calcium carbonate; acidity agents such as citric acid, tartaric acid, and malic acid; dyes such as iron sesquioxide, yellow iron sesquioxide, and tar dyes; perfumes such as lemon, lemon lime, orange, pine, mint, and menthol; sweeteners such as saccharin sodium, glycyrrhizin dipotassium, aspartame, stevia, and thaumatin; and flavoring agents such as citric acid, sodium citrate, succinic acid, tartaric acid, fumaric acid, and glutamic acid.

Furthermore, examples of stabilizers include sugars and sodium sulfite. Examples of the sugars include: monosaccharides such as glucose, fructose, xylitol, fucose, and galactose; disaccharides such as maltose, sucrose, lactose, lactulose, and melibiose; oligosaccharides such as fructooligosaccharide, galactooligosaccharide, and lactooligosaccharide; and polysaccharides such as dextran. Examples of preservatives include p-hydroxybenzoate ester, benzyl alcohol, chlorocresol, phenethyl alcohol, and benzethonium chloride. Examples of chelating agents include sodium edetate and sodium citrate. Examples of the antioxidants include sodium sulfite, sodium hydrogen sulfite, sodium ascorbate, and sodium thiosulfate.

Examples of dosage forms of a drug according to the present invention include: oral preparations such as tablets, capsules (including soft capsules, microcapsules, and enteric-coated capsules), powders, granules, and syrups; and parenteral preparations such as injections (e.g., hypodermic injections, intravenous injections, intramuscular injections, and intraperitoneal injections), external preparations (e.g., transnasal administration preparations, transcutaneous preparations, and ointments), suppositories (e.g., rectal suppositories and vaginal suppositories), pellets, drops, and sustained-release preparations (e.g., sustained-release microcapsules). The drug according to the present invention particularly preferably has the dosage form of an injection.

The dose of the liposome preparation according to the present invention differs depending on the type of the physiologically active substance (intended substance) carried by the liposome, the dosage form of the drug, the type of disease to be treated, the severity of conditions and disease, the age, sex, or body weight of a patient, an administration method, and so on and therefore, cannot be generalized. However, physicians can comprehensively assess the situations and determine the dose.

The administration route of the liposome preparation according to the present invention is not particularly limited and may be oral administration or parenteral administration depending on the forms of the drug according to the present invention as described above. The preferable embodiment of the present invention is parenteral administration. For example, when the drug according to the present invention is an injection, the administration route thereof can be exemplified by medically appropriate administration modes such as intraarticular injection, intravenous injection, hypodermic injection, intracutaneous injection, intramuscular injection, or intraperitoneal injection.

Hereinafter, the present invention will be described in detail with reference to Examples. However, the technical scope of the present invention is not intended to be limited to Examples below.

Example 1

In Example 1, a liposome having connexon consisting of connexin 43 (hereinafter, Cx43) was first constructed by in-vitro protein synthesis in the presence of the liposome (see FIG. 1). Specifically, an organic solvent (chloroform:methanol=2:1) solution of phosphatidylcholine derived from egg yolk was initially placed in a test tube, followed by solvent evaporation by vacuum drying. Thereby, a lipid film could be formed on the internal surface of the test tube.

Next, an in-vitro protein synthesis solution and a Cx43 gene-encoding plasmid were added into the test tube having the lipid film on the internal surface and left standing at 30° C. for 90 minutes. The in-vitro protein synthesis solution is a solution in which a Cx43-encoding plasmid with a T7 promoter is added in an amount of 1 μg per 50 μL of an in-vitro solution to a mixture solution of rabbit reticulocyte lysates (kit product in the form of master mix) containing RNA polymerase, amino acids serving as raw materials, an RNase inhibitor, and so on and adjusted to the final concentration of lipid (raw material for the liposome) of 5 mM. In this example, the plasmid used comprised an EGFP-encoding sequence fused with a Cx43 coding region.

Figure 2:
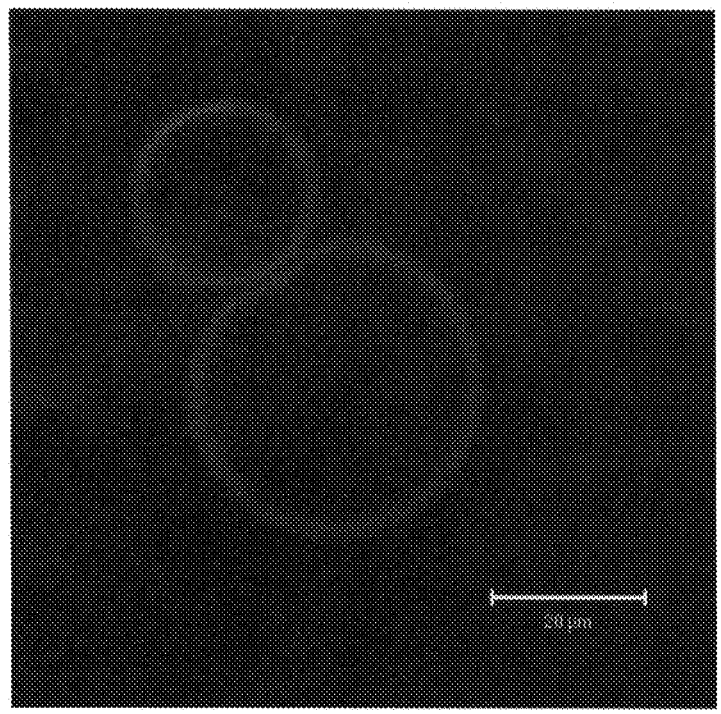
FIG. 2 is a photograph taken from an EGFP-incorporated liposome synthesized by in-vitro protein synthesis.

This treatment brought about liposome formation and Cx43 protein expression within the test tube and could construct a liposome having connexon consisting of Cx43 within the test tube. FIG. 2 shows a result of observing the constructed liposome (observed at an excitation wavelength: 488 nm and a fluorescence wavelength: 505 to 530 nm) with an inverted microscope IX-70 manufactured by Olympus Corp. As can be seen from FIG. 2, the fluorescence of EGFP could be observed within the lipid membrane according to this example.

Figure 3:
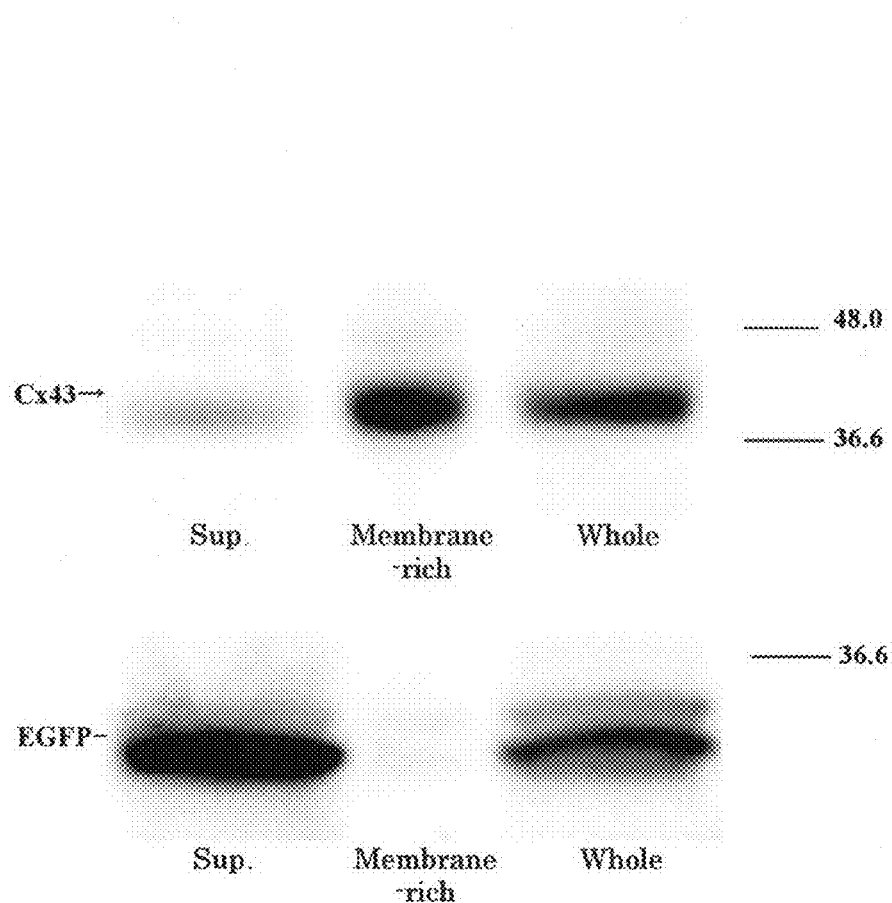
FIG. 3 is an electrophoretogram showing a result of studying connexin-containing and EGFP-containing fractions by use of a liposome in which connexin 43 is incorporated in the membrane and a liposome in which EGFP is incorporated in the membrane.

Next, Cx43- and EGFP-containing liposome solutions were separately ultracentrifuged at 53000 rpm at 4° C. for 30 minutes and separated into a lipid membrane fraction and a soluble fraction. FIG. 3 shows a result of studying these components by western blotting. As can be seen from FIG. 3, the water-soluble protein EGFP was mostly detected in the soluble fraction, whereas the Cx43 proteins were detected in larger amounts (80 to 90%) in the lipid membrane fraction. This suggested that Cx43 spontaneously move to a lipid membrane.

Example 2

In Example 2, the substance transfer between a liposome having connexon and cells was studied.

The transfer of intracellular substances into the liposome having connexon was initially studied. The cells used were U2OS osteosarcoma cells carrying constantly expressed Cx43, which were prepared by pretreatment with calcein-AM (colorless; manufactured by Molecular Probes). The liposome was prepared in the same way as in Example 1 except that a plasmid used had no EGFP-encoding sequence and had a Cx43 coding region.

Figure 4:
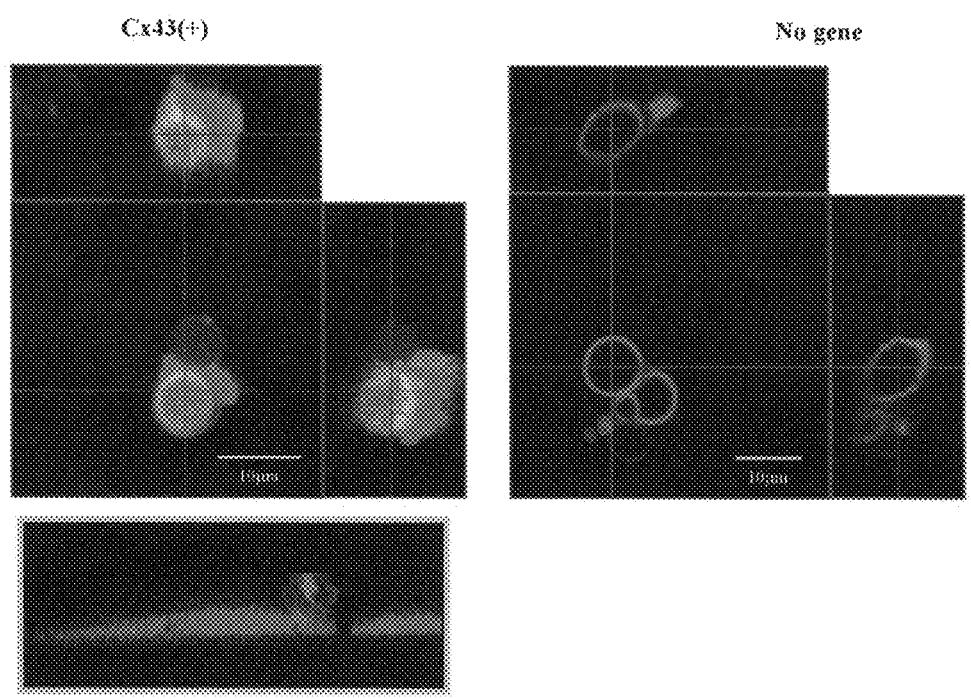
FIG. 4 is a photograph showing a result of injecting into a cell, calcein within a liposome in which connexin 43 is incorporated in the membrane.

One hour after the pretreatment, the liposome carrying expressed Cx43 was added to the culture solution. Two hours after the addition, calcein (green fluorescence) hydrolyzed within the cells was observed with a confocal laser scanning microscope to be also transferred into the liposome (FIG. 4 "Cx43(+)"). On the other hand, the transmission of calcein into a liposome having no Cx43 expression was not confirmed (FIG. 4 "No gene"). The confocal laser scanning microscope used was LSM510META manufactured by Carl Zeiss, with which calcein was observed at an excitation wavelength of 488 nm and a fluorescence wavelength of 505 to 530 nm. Moreover, Texas Red contained in the lipid membrane components was observed at an excitation wavelength of 543 nm and a fluorescence wavelength of 560 nm.

Figure 5:
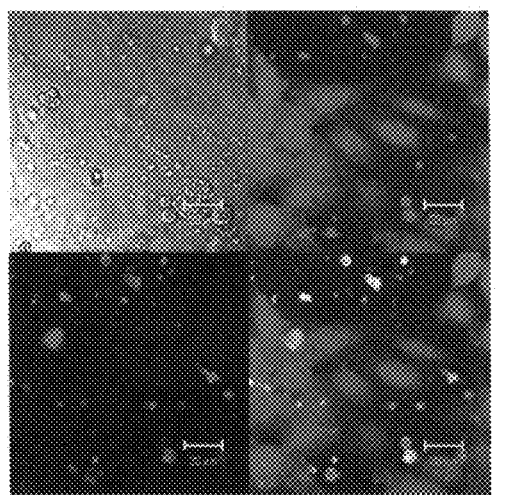
FIG. 5 is a photograph showing a result of injecting into a cell, calcein within a liposome in which connexin 43 is incorporated in the membrane.
Figure 5:
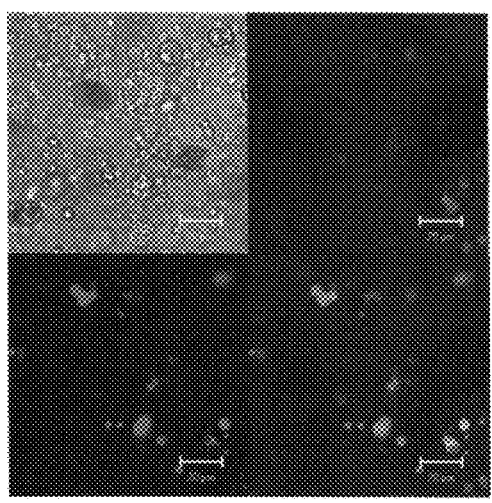

Next, in this Example, the transfer of a substance within the liposome having connexon into cells was studied. In this Example, the liposome used was constructed in the same way as in Example 1 except that a solution used contained 10 mM calcein (manufactured by Molecular Probes). The liposome used in this Example has connexon consisting of Cx43 and also has calcein therewithin. FIG. 5 shows a result of taking a picture of U2OS cells two hours after the addition of the liposome thus constructed to the culture solution of U2OS carrying expressed Cx43 (FIG. 5 "Cx-U2OS/Cx-Lipo"). The same experiment was performed as a comparative example using a liposome having no Cx43 expression. As a result, calcein transfer into the cells was not confirmed (FIG. 5 "Cx-U2OS/noGENE-Lipo").

Thus, it was demonstrated as shown in FIGS. 4 and 5 that the use of the liposome having connexon very efficiently performs the substance transfer between the liposome and cells.

Example 3

In Example 3, the introduction of a particular peptide into cells was attempted using a liposome having connexon. Simultaneously, the regulation of physiological activity within the cells by the action of the peptide was studied.

Figure 6:
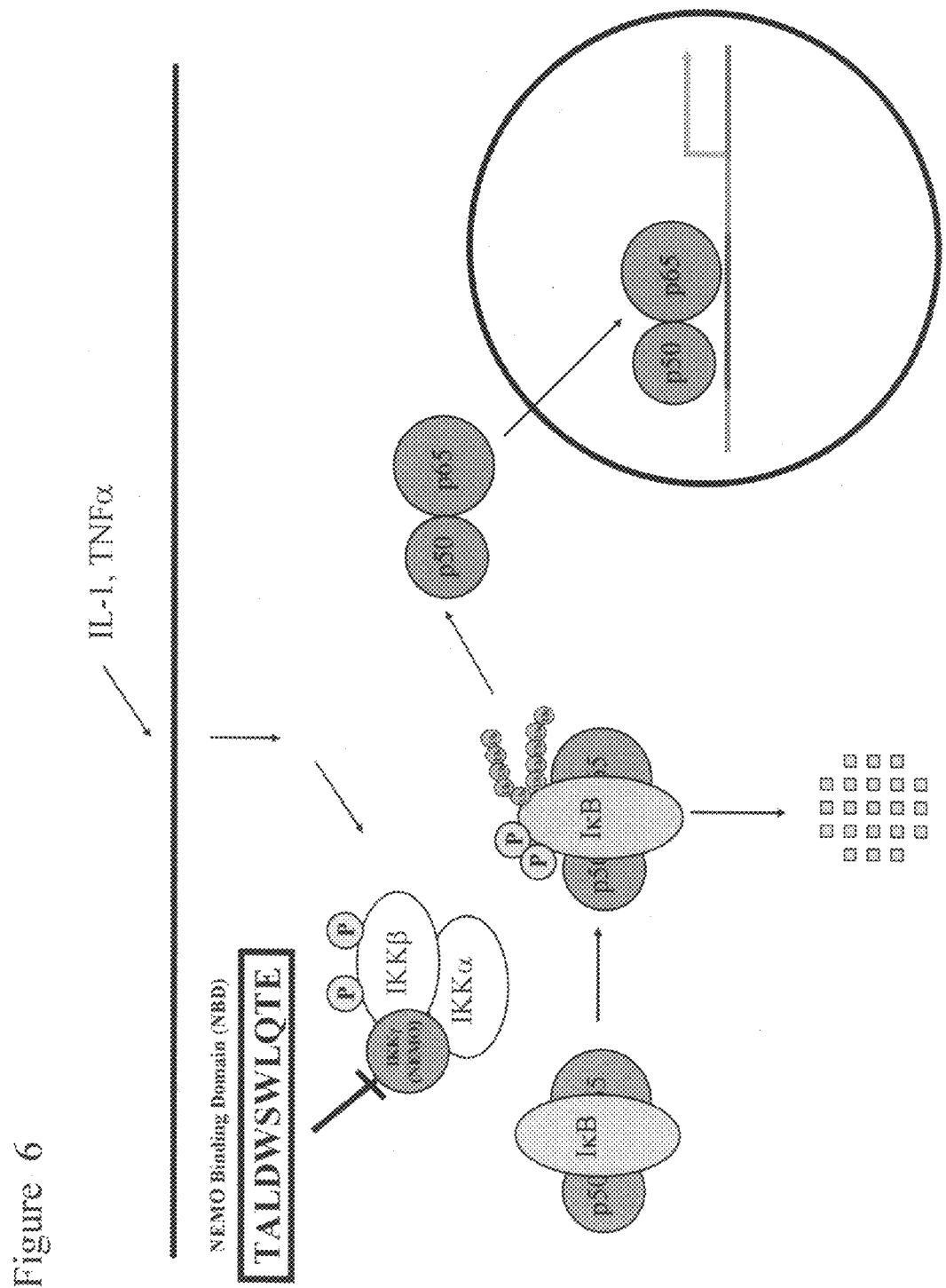
FIG. 6 is a diagram schematically showing gene expression regulation by a NEMO-binding domain.

As schematically shown in FIG. 6, an IKK complex is activated by IL-1β stimulation or the like and thereby phosphorylates IκB. The phosphorylated IκB is further polyubiquitinated and degraded by a pathway in a proteasome system. As a result, the suppressive effect of IκB on NFκB (p50+p65) disappears. The nuclear-imported NFκB increases the transcriptional activity of a gene of interest. A NEMO Binding Domain ((SEQ ID NO:3); hereinafter, NBD) is known to be a sequence present in the C-terminus of IKKβ, one component in the IKK complex, and be necessary for binding with IKKγ (NEMO). The solubilized NBD oligopeptide originally suppresses normal IKK functions through its competitive inhibition of the binding of IKKβ with NEMO and thereby suppresses the nuclear import of NFκB and the transcription of a gene of interest. This peptide cannot permeate into cells by itself and does not act. Thus, in this example, a liposome having connexon consisting of Cx43 was used to attempt the administration of the NBD peptide into cells via a gap junction.

Specifically, the U2OS cells used in Example 2 was initially cultured until 80 to 90% density in a 10-cm culture dish, on which a liposome containing the NBD peptide was then allowed to act for 12 hours. In this example, the liposome used was constructed in the same way as in Example 1 except that a solution used contained 50 μL of the NBD peptide.

Figure 7A:
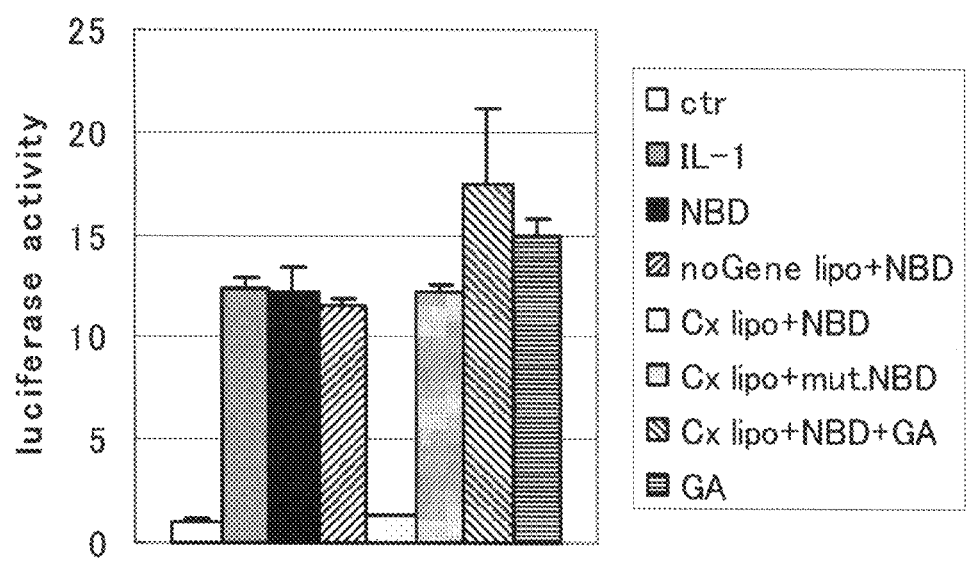
FIGS. 7A and 7B are respectively a characteristic diagram showing an NF-kB reporter gene assay result.
Figure 7B:
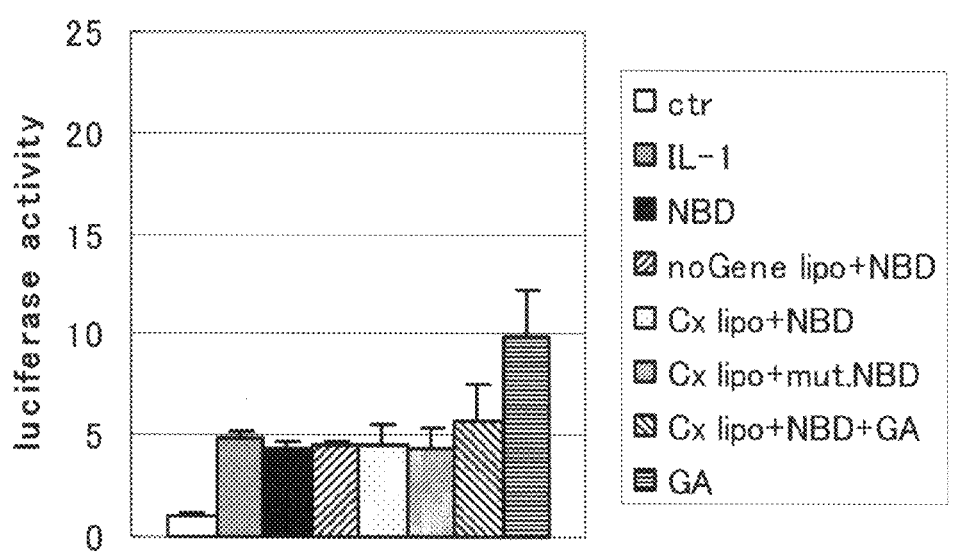

Then, IL-1β was allowed to act thereon for 24 hours, followed by measurement of intracellular luciferase activity (FIGS. 7A and 7B). The administration of the NBD peptide using the Cx43-expressing liposome suppressed IL-1β stimulation-induced rises in NFκB activity in the cells carrying expressed Cx43 (FIG. 7A). This suppressive effect was not confirmed when the liposome was not used, when administration was performed using a liposome having no Cx43 expression, and when a peptide having the NBD sequence to which a mutation was added was administered (FIG. 7B). Moreover, pretreatment using a gap junction inhibitor 18β-glycyrrhetinic acid (GA) suppressed the NBD effect. Furthermore, the same experiment was performed using U2OS having no Cx43 expression. As a result, NFκB activity was not suppressed even when NBD was administered using the Cx43-expressing liposome.

Figure 8:
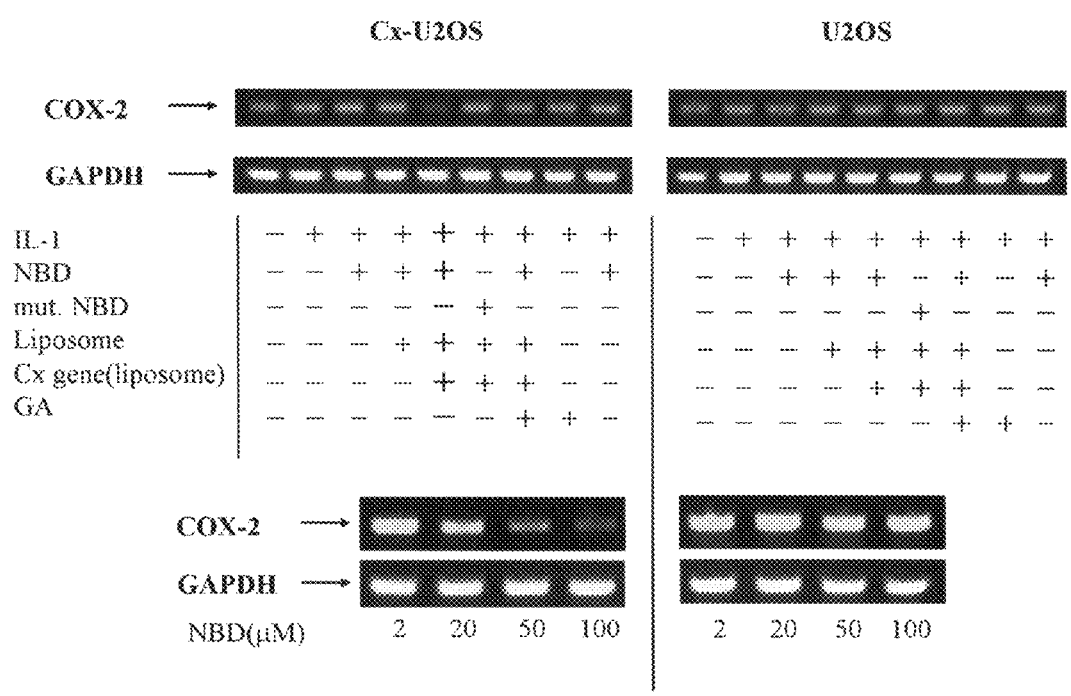
FIG. 8 is a characteristic diagram showing a result of detecting COX-2 mRNA.

FIG. 8 shows a result of studying COX-2 expression by an RT-PCR method by use of NBD peptide administration in the same way. In FIG. 8, "Cx-U2OS" denotes a result obtained using a liposome having connexon, and "U2OS" denotes a result obtained using a liposome having no connexon. As can be seen from FIG. 8, the administration of NBD using the Cx43-expressing liposome suppressed IL-1 stimulation-induced rises in COX-2 expression. This suppressive effect depended on NBD peptide concentrations. Moreover, the suppression of COX-2 expression was not confirmed in the administration of NBD alone, the administration of NBD using the liposome having no Cx43 expression, administration after pretreatment with GA, and the administration of mutant NBD. Furthermore, the NBD effect was not confirmed on U2OS having no Cx43 expression.

Thus, the results shown in FIGS. 7 and 8 revealed that the use of the liposome according to the present invention can efficiently introduce a desired substance into cells and as a result, can regulate gene expression and so on within the cells. These findings revealed that the liposome according to the present invention comprises a pharmaceutical composition or the like therewithin and can thereby provide treatment methods effective for various diseases.

Example 4

In Example 4, the substance (calcein in this example) transfer between a liposome having connexon and cells was studied by the same experiment as in Example 2 except that mouse MC3T3-E1 osteoblasts were used instead of the U2OS osteosarcoma cells. The MC3T3-E1 cells used in this example are cells carrying constantly expressed Cx43.

Figure 9:
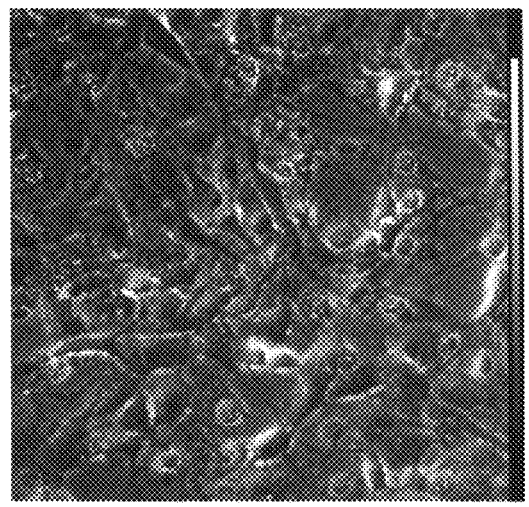
FIG. 9 is a transmitted light photograph showing a result of injecting into a cell, calcein within a liposome in which connexin 43 is incorporated in the membrane.
Figure 10:
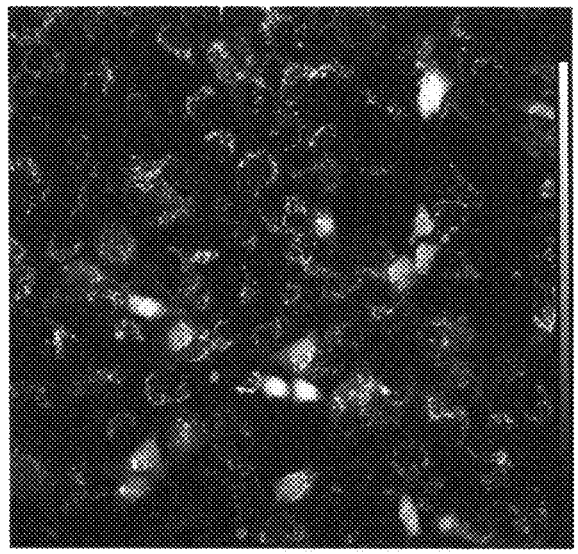
FIG. 10 is a fluorescence photograph showing a result of injecting into a cell, calcein within a liposome in which connexin 43 is incorporated in the membrane.

In this example, the liposome used having connexon was prepared in the same way as in Example 1 using an organic solvent in which egg yolk phosphatidylcholine (EPC), dioleoylphosphatidylethanolamine (DOPE), and cholesterol (Chol) were adjusted to a ratio of EPC:DOPE:Chol=6:1:3. FIG. 9 shows a result of taking a photograph of transmitted light two hours after the addition of the liposome thus constructed to the culture solution of MC3T3-E1. FIG. 10 shows a result of taking a photograph of fluorescence. As can be seen from FIGS. 9 and 10, calcein transfer into the cells could also be confirmed in this Example using the MC3T3-E1 cells carrying constantly expressed Cx43. By contrast, the same experiment was performed as a comparative example using a liposome having no Cx43 expression. As a result, calcein transfer into the cells was not confirmed (not shown).

Industrial Applicability

The present invention can introduce a connexon having a gap junction function into a liposome membrane and can therefore provide a liposome very excellent in substance injection efficiency used in so-called drug delivery systems and general biochemical experiments. Moreover, the present invention can provide a method for injecting a substance to a cell with very excellent substance injection efficiency. The present invention greatly contributes to the treatments of a variety of diseases using drug delivery systems.

All publications, patents, and patent applications cited herein are incorporated herein by reference in their entirety.

---

The invention claimed is:

1. A liposome comprising:
   a connexon composed of oligomeric connexin co-translationally inserted into a connexon-free phospholipid bilayer of said liposome,
   wherein said connexin is synthesized by in-vitro protein synthesis and assembled into oligomers in the phospholipid bilayer of said liposome,
   wherein said connexon forms a gap junction with an opposing cell, and
   wherein the liposome maintains an intended substance without transmitting it to the outside before formation of said gap junction.

2. The liposome according to claim 1, wherein said connexon comprises connexin 43.

3. The liposome according to claim 1, wherein said phospholipid bilayer further comprises a membrane protein having an ability to bind to a particular cell.

4. The liposome according to claim 1, further comprising the intended substance within the interior of said liposome for transfer to said opposing cell after formation of a gap junction between said liposome and said cell.

5. The liposome according to claim 4, characterized in that the intended substance is mainly composed of a component of 1500 or lower in molecular weight.

6. A method for injecting a substance into a cell, comprising:
   bringing a liposome according to claim 1 into contact with an isolated cell or cultured cell; and
   injecting the intended substance into the isolated cell or cultured cell.

7. A method for treating disease, comprising the step of administering a liposome according to claim 4.

8. The liposome of claim 1, wherein said oligomeric connexin is homomeric.

9. The liposome according to claim 4, wherein the intended substance comprises a physiologically active component.

* * * * *

UNITED STATES PATENT AND TRADEMARK OFFICE
CERTIFICATE OF CORRECTION

PATENT NO. : 9,023,384 B2  
APPLICATION NO. : 11/666736  
DATED : May 5, 2015  
INVENTOR(S) : Ikuo Morita, Kazunari Akiyoshi and Shinichiro Nomura It is certified that error appears in the above-identified patent and that said Letters Patent is hereby corrected as shown below:

On the Title Page,

"(73)   Assignees:   Tokyo Medical and Dental University, Tokyo (JP); Dai Nippon Printing Co., Ltd., Tokyo (JP)", should be --(73)   Assignees:   National University Corporation Tokyo Medical and Dental University, Tokyo (JP); Dai Nippon Printing Co., Ltd., Tokyo (JP)--.

Signed and Sealed this  
Twenty-second Day of December, 2015

Michelle K. Lee  
*Director of the United States Patent and Trademark Office*